United States Patent [19]

Jansen et al.

[11] Patent Number: 5,183,939
[45] Date of Patent: Feb. 2, 1993

[54] PROCESS FOR THE RACEMIZATION OF OPTICALLY ACTIVE 1-ARYL-ALKYLAMINES

[75] Inventors: Johannes R. Jansen, Monheim; Martin Littmann, Cologne, both of Fed. Rep. of Germany

[73] Assignee: Bayer Aktiengesellschaft, Leverkusen, Fed. Rep. of Germany

[21] Appl. No.: 796,109

[22] Filed: Nov. 21, 1991

[30] Foreign Application Priority Data

Dec. 1, 1990 [DE] Fed. Rep. of Germany ....... 4038356

[51] Int. Cl.$^5$ .......................................... C07C 209/00
[52] U.S. Cl. .................................................. 564/302
[58] Field of Search ........................................ 564/302

[56] References Cited

U.S. PATENT DOCUMENTS

| | | | |
|---|---|---|---|
| 2,152,976 | 4/1939 | Scheuing et al. | 564/302 |
| 3,970,700 | 7/1976 | Nagase et al. | 564/302 |
| 3,991,077 | 11/1976 | Uzuki et al. | 564/498 |
| 4,158,016 | 6/1979 | Nagase et al. | 260/570.5 R |
| 4,246,424 | 1/1981 | Nagase et al. | 560/38 |
| 4,252,744 | 2/1981 | Bison et al. | 564/302 |
| 4,377,587 | 3/1983 | Hubele et al. | 564/192 |

FOREIGN PATENT DOCUMENTS

| | | |
|---|---|---|
| 0300313 | 7/1988 | European Pat. Off. . |
| 0341475 | 4/1989 | European Pat. Off. . |
| 2441651 | 1/1973 | Fed. Rep. of Germany . |
| 2903589 | 8/1980 | Fed. Rep. of Germany ...... 564/302 |

OTHER PUBLICATIONS

Windholz et al., *The Merck Index*, Merck & Co., Rahway, N.J. (1983) p. 520.
Abstract of DE 2,442,845 Sumitomo (1975).
Abstract of DE 2,851,039 BASF (1980).

*Primary Examiner*—Richard L. Raymond
*Assistant Examiner*—P. O'Sullivan
*Attorney, Agent, or Firm*—Sprung Horn Kramer & Woods

[57] ABSTRACT

A new process for the racemization of optically active 1-aryl-alkylamines of the formula (I)

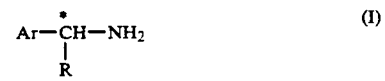

in which
  Ar represents optionally substituted aryl and
  R represents alkyl,
which is characterized in that compounds of the formula (I) which largely have the R- or S-configuration at the carbon atom marked by * are reacted with metal alkoxides in dimethyl sulphoxide, optionally in the presence of appropriate alcohols, at temperatures between 0° C. and 200° C.

4 Claims, No Drawings

PROCESS FOR THE RACEMIZATION OF OPTICALLY ACTIVE 1-ARYL-ALKYLAMINES

The invention relates to a new process for the preparation of racemic mixtures of optically active 1-aryl-alkylamines of the formula (I) by treating with metal alkoxides in dimethyl sulphoxide.

Some optically active 1-aryl-alkylamines are known as commercial synthesis chemicals and some as useful organic intermediates for agrochemicals, such as herbicides or fungicides or for medicaments (cf. EP-A 300,313; EP-A 341,475). Thus, the optical antipodes of the 1-aryl-alkylamines in isolated form are also used as salt-forming agents for the separation of racemic mixtures of optically active acids, as they can be easily synthesized and resolved into the antipodes in a simple manner. Compared to the naturally occurring alkaloids, which were earlier used for this purpose, they have the advantage of being available for industrial processes in any desired amount.

In general, the optically active compounds of the general formula (I) are prepared in the form of racemic mixtures, which are then resolved into their optical antipodes. After the separation of the useful optical antipode, the undesired antipode is racemized again and the racemate is resolved into the optical antipodes once more. The racemization is therefore used indirectly for the preparation of desired optically active compounds.

Processes for the racemization of optically active 1-aryl-alkylamines are already known. Essentially, these racemizations are carried out in the presence of metal-containing catalysts, for example in the presence of naphthalene sodium or anthracene sodium (cf. DE-OS (German Published Specification) 2,441,651), in the presence of sodium or potassium and if appropriate additionally of their hydroxides on alumina (cf. DE-OS (German Published Specification) 2,442,854; JP-A 50/050,317 —cited in Chem. Abstracts 83, 96701), in the presence of sodium hydride or sodium amide (cf. DE-OS (German Published Specification 2,348,801), or alternatively in the presence of hydrogen/Raney cobalt (cf. DE-OS (German Published Specification) 2,851,039).

The known racemization processes, however, are essentially not highly suitable for use on the industrial scale, be it because of the unsatisfactory yield or the insufficient quality of the products, or be it because of industrially disadvantageous catalysts, whose use is affected by high safety risks and/or by working-up problems.

A process for the racemization of optically active 1-aryl-alkylamines of the general formula (I)

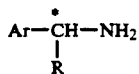

in which
Ar represents optionally substituted aryl and
R represents alkyl,
has now been found, which is characterized in that compounds of the formula (I) which largely have the R- or S-configuration at the carbon atom marked by * are reacted with metal alkoxides in dimethyl sulphoxide, optionally in the presence of the appropriate alcohols, at temperatures between 0° C. and 200° C.

The optically active compounds of the formula (I) can contain the R- and/or S-form in any proportion, i.e. the pure forms or also mixtures of varying composition.

Surprisingly, the optically active 1-aryl-alkylamines of the formula I can be completely racemized simply and rapidly using industrially advantageous substances by the process according to the invention. It is particularly to be emphasized that the racemization occurs virtually without side reactions even with halogen-substituted compounds of the formula (I), while dehalogenations and/or oligomerizations would occur as interfering side reactions with these compounds using the known catalysts.

In the general formula (I), Ar represents aryl, preferably phenyl or naphthyl, which is optionally monosubstituted to pentasubstituted by identical or different substituents, the possible substituents preferably being selected from the series comprising halogen, and alkyl, haloalkyl, alkoxy, haloalkoxy, alkylthio, alkylsulphinyl or alkylsulphonyl in each case having 1 to 4 carbon atoms and in each case being straight-chain or branched.

Ar in particular represents phenyl or naphthyl, which are each optionally monosubstituted to trisubstituted by fluorine, chlorine, bromine, methyl, trifluoromethyl, methoxy and/or trifluoromethoxy, very particularly 4-chloro-phenyl.

R in the formula (I) represents straight-chain or branched alkyl, preferably having 1 to 6, in particular 1 to 3 carbon atoms, very particularly methyl.

The process according to the invention is in particular carried out to racemize 1-(4-chloro-phenyl)-ethylamine.

The compounds of the formula (I) to be employed as starting substances in the process according to the invention, which largely have the R- or S-configuration on the carbon atom marked by *, are known and/or can be obtained by processes which are known per se; they are in general obtained as coupling products in the resolution of the racemate of compounds of the formula (I) (cf. EP-A 341,475).

Metal alkoxides which are used in the process according to the invention are preferably alkali metal, alkaline earth metal or earth metal alkoxides having straight-chain or branched alkyl groups which contain 1 to 8 carbon atoms. Particularly preferred metal alkoxides are alkali metal alkoxides having 1 to 6 carbon atoms. Examples which may be mentioned are:

potassium ethoxide, isopropoxide, sec-butoxide, tert-butoxide, sec-pentoxide and tert-pentoxide (tert-amylate).

The reaction temperatures can be varied within a relatively large range in the process according to the invention. In general, the reaction is carried out at temperatures between 0° C. and 200° C., preferably at temperatures between 20° C. and 120° C.

The process according to the invention is in general carried out under normal pressure. However, it is also possible to work at elevated or reduced pressure - in general between 10 hPa and 10,000 hPa.

To carry out the process according to the invention, in general between 0.01 and 10 mol, preferably between 0.05 and 1.0 mol, of metal alkoxide and in general between 0.5 and 20 mol, preferably between 1.0 and 10 mol, of dimethyl sulphoxide are employed relative to 1 mol of starting compound of the formula (I).

In a preferred embodiment of the process according to the invention, the optically active starting compound of the formula (I) is mixed with dimethyl sulphoxide at room temperature (about 20° C.), and the mixture is optionally heated to a higher temperature and treated with the metal alkoxide, which is optionally dissolved in an appropriate alcohol.

After the racemization reaction has occurred, the mixture is worked up by customary methods.

For example, the alkoxide is neutralized with hydrochloric acid or the hydrochloride of the racemic amine of the formula (I) and the racemized product of the formula (I) is isolated by distillation under reduced pressure.

PREPARATION EXAMPLES

EXAMPLE 1

1500 g (9.65 mol) of 1-(4-chloro-phenyl)-ethylamine (purity: 95%, $^1$H-NMR; S/R=80:20, chiral GC) are mixed with 1800 g (23.1 mol) of dimethyl sulphoxide and this mixture is heated to 80° C. in the course of 20 minutes. A further 300 g (3.85 mol) of dimethyl sulphoxide are kept ready in a dropping funnel as a "temperature buffer". 162 g (1.45 mol) of potassium tert-butoxide are then added to the mixture in the course of 1 minute, whereupon the internal temperature rises to about 90° C. A further rise in the internal temperature is prevented by metering in about 150 g of the abovementioned dimethyl sulphoxide supply. The reaction mixture is kept at 85° C. to 90° C. for 60 minutes, then cooled to about 20° C. and treated with 245 ml of 6 N hydrochloric acid. The racemization product is isolated by distillation in a steam-jet vacuum.

1410 g (94% of theory) of 1-(4-chloro-phenyl)-ethylamine of boiling point 125° C./2 hPa are obtained (purity:>95%, $^1$H-NMR; S/R=50:50).

EXAMPLE 2

470 g (3.02 mol) of (S)-1-(4-chloro-phenyl)-ethylamine are mixed with 611 g (7.83 mol) of dimethyl sulphoxide; 37.8 g (0.3 mol) of potassium tert-pentoxide (potassium tert-amylate) are then added thereto and the mixture is heated to 100° C. in the course of 25 minutes. After 45 minutes at 100° C., the mixture is cooled to 0° C. and 50 ml of 6 N hydrochloric acid are rapidly added dropwise. The racemization product is isolated by distillation in a steam-jet vacuum.

432 g (92% of theory) of (R/S)-1-(4-chloro-phenyl)-ethylamine of boiling point 120° C./1.5 hPa are obtained.

EXAMPLE 3

121 g (1.0 mol) of (R)-1-phenyl-ethylamine are mixed with 200 g (2.55 mol) of dimethyl sulphoxide; 16.8 g (0.15 mol) of potassium tert-butoxide are then added thereto and the mixture is heated to 90° C. for 60 minutes. After cooling to 20° C. it is treated with 20 ml of 6 N hydrochloric acid and the racemization product is isolated by distillation under reduced pressure.

106.5 g (88% of theory) of (R/S)-1-phenyl-ethylamine are obtained.

In Examples (1) to (3), the compound of the formula (I) having the R-configuration in each case corresponds to the dextrorotatory antipodes ("(+)-form") and the compound having the S-configuration corresponds to the levorotary antipode ("(−)-form").

We claim:

1. A process for the racemization of an optically active 1-aryl-alkylamine, which comprises reacting an optically active amine of the formula (I)

in which
C is an asymmetric carbon atom,
Ar is phenyl or naphthyl which is optionally monosubstituted to pentasubstituted by identical or different substituents selected from the group consisting of halogen, and alkyl, haloalkyl, alkoxy, haloalkoxy, alkythio, alkylsulphinyl or alkylsulphonyl in each case having 1 to 4 carbon atoms and in each case being straight-chain or branched, and
R is alkyl having 1 to 6 carbons atoms,
with an alkali, alkaline earth metal or earth metal alkoxide, in dimethyl sulphoxide at a temperature from 0° to 200° C.

2. A process according to claim 1, wherein the reaction is effected in the presence of an alcohol in addition to the dimethyl sulphoxide.

3. A process according to claim 1, wherein the optically active amine is in pure form.

4. A process according to claim 1, wherein
Ar is phenyl or naphthyl which is monosubstituted to trisubstituted by identical or different substituents selected from the group consisting of fluorine, chlorine, bromine, methyl, trifluoromethyl, methoxy and trifluoromethoxy, and
R is straight-chain or branched alkyl having 1 to 3 carbon atoms.

* * * * *